United States Patent
Bohner et al.

(10) Patent No.: US 9,125,966 B2
(45) Date of Patent: Sep. 8, 2015

(54) BONE REPAIR MATERIAL

(75) Inventors: Marc Bohner, Grenchen (CH); Andrea Montali, Basel (CH); Yvonne Bruderer, Zofingen (CH)

(73) Assignees: DR. H.C. ROBERT MATHYS STIFTUNG, Bettlach (CH); DEPUY SYNTHES PRODUCTS, INC., Raynham, MA (US)

( * ) Notice: Subject to any disclaimer, the term of this patent is extended or adjusted under 35 U.S.C. 154(b) by 1779 days.

(21) Appl. No.: 12/093,544

(22) PCT Filed: Nov. 15, 2005

(86) PCT No.: PCT/CH2005/000673
§ 371 (c)(1),
(2), (4) Date: May 13, 2008

(87) PCT Pub. No.: WO2007/056872
PCT Pub. Date: May 24, 2007

(65) Prior Publication Data
US 2009/0220475 A1    Sep. 3, 2009

(51) Int. Cl.
| A61K 8/02 | (2006.01) |
| A61K 9/00 | (2006.01) |
| A61L 24/00 | (2006.01) |
| A61L 24/02 | (2006.01) |
| A61L 27/12 | (2006.01) |
| A61L 27/42 | (2006.01) |

(52) U.S. Cl.
CPC ............. *A61L 24/0063* (2013.01); *A61L 24/02* (2013.01); *A61L 27/12* (2013.01); *A61L 27/425* (2013.01); *A61L 2430/02* (2013.01)

(58) Field of Classification Search
CPC ............................. A61K 8/022; A61K 9/0019
USPC .......................................................... 424/400
See application file for complete search history.

(56) References Cited

U.S. PATENT DOCUMENTS

| 5,149,368 | A | * | 9/1992 | Liu et al. ....................... 424/602 |
| 5,902,839 | A | * | 5/1999 | Lautenschlager et al. .... 523/115 |
| 6,013,591 | A | * | 1/2000 | Ying et al. ........................ 501/1 |
| 6,713,527 | B2 | * | 3/2004 | Bond et al. ..................... 523/118 |
| 6,719,993 | B2 | * | 4/2004 | Constantz ....................... 424/423 |
| 2002/0076429 | A1 | * | 6/2002 | Wironen et al. ............... 424/426 |
| 2002/0095213 | A1 | * | 7/2002 | Bakker et al. .............. 623/13.11 |
| 2005/0241535 | A1 | | 11/2005 | Bohner |

FOREIGN PATENT DOCUMENTS

| DE | 3934803 | * | 4/1991 |
| WO | 99/20237 | | 4/1999 |
| WO | 00/45870 A1 | | 8/2000 |
| WO | 03/082365 | | 10/2003 |
| WO | 2005/115488 A2 | | 12/2005 |

OTHER PUBLICATIONS

"Pyrophosphate", Wikipedia, the free encylcopedia, 2014.*
Bohner, M. et al.; "Technological issues for the development of more efficient calcium phosphate bone cements: A critical assessment"; Biomaterials, Elsevier Science Publishers BV., Barking, Great Britain; vol. 26, No. 33; Nov. 2005; pp. 6423-6429; XP004989098.
Arts, J. J. Chris et al.; "The use of a bioresorbable nano-crystalline hydroxyapatite paste in acetabular bone impaction grafting"; Biomaterials, Elsevier Science Publishers BV., Barking, Great Britain; vol. 27, No. 7; Mar. 2006; pp. 1110-1118; XP005152652.
Arts, J.J. C. et al.; "Cemented cup stability during lever-out testing after acetabular bone impaction grafting with bone graft substitutes mixes containing morselized cancellous bone and tricalcium phosphate—hydroxyapatite granules"; Proceedings of the Institution of Mechanical Engineers; Part H; Journal of Engineering in Medicine; Jul. 2005; vol. 219, No. 4; Jul. 2005; pp. 257-263; XP009069581.
Fernandez, Enrique. et al.; "Modulation of porosity in apatitic cements by the use of alpha-tricalcium phosphate-calcium sulphate dehydrate mixtures"; Biomaterials, Elsevier Science Publishers BV., Barking, Great Britain; vol. 26, No. 17; Jun. 2005; pp. 3395-3404; XP004696086.
Apelt, D. et al.; In vivo behavior of three different injectable hydraulic calcium phosphate cements; Biomaterials, Elsevier Science Publishers BV., Barking, Great Britain; vol. 25, No. 7-8; Mar. 2004; pp. 1439-1451; XP004475089.

* cited by examiner

*Primary Examiner* — Ruth Davis
(74) *Attorney, Agent, or Firm* — Rankin, Hill & Clark LLP

(57) ABSTRACT

The bone repair material comprises the following components:
A) a first granular component with a diameter larger than 20 μm chosen from the group of: calcium phosphate, calcium pyrophosphate, or calcium sulfate dihydrate;
B) a second component chosen from the group of apatite powder with a particle diameter smaller than 1 μm, (preferably smaller than 100 nm); and
B) a third component comprising water or an aqueous solution, whereby
C) the volume fraction of the second and third component represents at least 35 volume-% of the total bone repair material.

30 Claims, No Drawings

BONE REPAIR MATERIAL

BACKGROUND OF INVENTION

1. Field of Invention

The invention relates to a bone repair material that is useful in the repair of bone defects, in particular in the repair of defects filled with aqueous body fluids such as blood.

2. Description of Related Art

From WO03/082365 a kneadable and formable bone replacement mass is known based on ceramic particles having a diameter in the range of 0.1 mm to 5.6 mm suspended in a hydrogel. This mass has the disadvantage that hydrogels for human use are very expensive. Another disadvantage connected with hydrogels is the fact that sterilization via gamma-irradiation destroys the polymer chain, hence reducing the average molecular weight and decreasing the polymer viscosity.

From the WO 99/20237 a stomatic composition based on hydroxyapatite nanoparticles is known which may include further components such as various abrasive materials (0 to 25%). These abrasive materials may consist of anhydrous dicalcium phosphate, dicalcium phosphate dihydrate, and calcium carbonate. However, there is no indication in this prior art document about the preferred size range for these abrasive materials. Also it does not mention the use of β-tricalcium phosphate. Moreover, this prior art cement is proposed only for use in the field of stomatology and not of bone repair. The main disadvantage of this known material is that it does not allow the surrounding bone cells to anchor and to proliferate.

From two articles of JJC Arts et al.:
"The use of a bioresorbable nano-crystalline hydroxyapatite paste in acetabular bone impaction grafting". Biomaterials, In Press, and
"Cemented cup stability during lever-out testing after acetabular bone impaction grafting with bone graft substitutes mixes containing morselized cancellous bone and tricalcium phosphate-hydroxyapatite granules" published in Proc Inst Mech Eng [H] 2005; 219:257-67, it is known that a nano-crystalline paste (40 weight-% water) can be combined with biphasic calcium phosphate granules (80% β-TCP, 20% HA). The latter authors used very large granule diameters, i.e. 1.5-2.0 mm, 4-6 mm, and 4-8 mm granules combined with a very small nano-crystalline paste content (up to 33 volume-%), because they wanted to use the granular paste for impaction grafting. Results showed however that a 33 volume-% paste content—for that special field of application—was too much to provide an adequate initial cup stability and therefore the authors were led to prefer lower contents in the region of 10% for the nano-crystalline paste. For these reasons the authors did not even consider the possibility of using a higher content (over the 33 volume-%) of nano-crystalline paste.

Accordingly, it is the principal object of the present invention to provide a bone repair material overcoming the above disadvantages and not being based on hydrogel.

BRIEF SUMMARY OF THE INVENTION

To achieve the above object the present invention relates to a bone repair material comprising:
A) a first granular component having a diameter larger than 20 μm selected from the group consisting of: calcium phosphate, calcium pyrophosphate and calcium sulfate dihydrate;
B) a second component consisting of apatite powder having a particle diameter smaller than 1 μm; and
C) a third component comprising water or an aqueous solution; whereby
D) the second component and the third component collectively represent at least 35 volume-% of the total bone repair material.

The advantages of the bone repair material according to the invention compared to the state of the art materials are the following:
compared to hydrogel-based putties they are much cheaper because there is no need to use an expensive hydrogel for human use;
compared to pure nanoparticle-liquid mixtures they offer the important advantage that the additional, comparatively large granules provide a scaffold on which bone cells can anchor and proliferate;
compared to the usual calcium phosphate cements (pastes/putties that harden within a short time after mixing fluid and powder components), the bone repair material according to the invention is much easier to use (no time-dependent properties) and to produce (relatively inert); and
the bone repair material (with no hydrogel present) can be sterilized without any problem by gamma irradiation.

DETAILED DESCRIPTION OF THE INVENTION

The first component can be chosen from the group of β-tricalcium phosphate, α-tricalcium phosphate, hydroxyapatite, tetracalcium phosphate, DCPD [dicalcium phosphate dihydrate $(CaHPO_4.2H_2O)$], DCP [dicalcium phosphate $(CaHPO_4)$], OCP [octocalcium phosphate $(Ca_8H_2(PO_4)_6.5H_2O)$], α-CPP [α-calcium pyrophosphate $(Ca_2P_2O_7)$], β-CPP [β-calcium pyrophosphate $(Ca_2P_2O_7)$], γ-CPP [γ-calcium pyrophosphate $(Ca_2P_2O_7)$], and CSD [calcium sulfate dihydrate $(CaSO_4.2H_2O)$]. Concerning these different compounds, the advantage of choosing specific compounds is the fact that the resorption rate of the paste can be modulated according to the clinical indication. For example, CSD is rapidly cleared from the body, whereas sintered hydroxyapatite particles would remain unresorbed for decades.

The diameter of the first granular component is typically larger than 50 microns and preferably larger than 100 microns. It is typically smaller than 1000 microns and preferably smaller than 200 microns.

In a special embodiment the fraction of the second and third component is in the range of 77 to 83 volume-% of the total bone repair material. If lower ratios are used (below 77%), the mixture becomes too brittle. If higher ratios are used (close to 83%) the mixture becomes elastic, moldable and well injectable.

The apatite powder may be chosen from the group of calcium-deficient hydroxyapatite, hydroxyapatite or fluoroapatite.

The first component comprises preferably a mixture of granules of different size, preferably in the form of several fractions of monodispersed granules. The size ratio of two neighboring size fractions should be larger than 1.4, preferably larger than 1.5.

In a further embodiment the granules of the first component are macroporous, preferably with a pore diameter superior to 0.05 mm. The advantage lies in the optimization of the mechanical and biological properties of the granules.

In a further embodiment the granules of the first component have a porosity of less than 90%. Higher porosities would lead to an undesirable granule fracturing during handling.

Typically the granules of said first component have an apparent volume smaller than 80%, preferably smaller than 30%. 80% meaning that the material volume "mv" present in a defect of volume "dv" corresponds to less than 80% of "dv". The volume of the material "mv" is calculated by dividing the material weight by the theoretical density of the material. Typically the apparent volume may be close 25%.

In a special embodiment the granules of the first component are spherical. In an other embodiment the granules of the first component are non-spherical and preferably concave. The advantage of the latter embodiment is that cells can more easily proliferate in concavities than convexities.

In a further embodiment the apatite powder comprises deagglomerated powder particles. Apatite powders are typically obtained by precipitation. Therefore, any precipitation method that enables the obtention of deagglomerated particles is of interest. The use of a nano- or micro-batch reactor (precipitation in a nano- or micro-volume) are of interest.

In a further embodiment the ratio between the third component expressed in milliliters and the sum of said first and second components expressed in grams is comprised in the range of 0.05 to 1.0 mL/g, preferably in the range of 0.1 to 0.7 mL/g. The volume ratio between the third and the first component may be in the range of 2.7-3.8 preferably between 3.0-3.4.

The bone repair material may further comprise an additive increasing the surface charge of the particles present in the formulation. Such additives may include a carboxylated compound, preferably having citrate or poly(carboxylated) ions, e.g. polyacrylic acid.

In a further embodiment the third component has a high ionic strength, typically 0.15 m or higher. This reduces the thickness of the electrical double layer present on the particle surface, hence reducing the repulsive interactions between the particles and hence increasing the stickiness of the resulting paste.

In a further embodiment the third component comprises a content of 0.1-1.0 w % of a hydrogel, preferably sodium hyaluronate.

The bone repair material may further comprise one or more drugs useful in the treatment of bone defects or bone diseases, in particular pharmaceutically or physiologically active substances. Specific examples would include antibacterial substances, anti-inflammatory drugs, drugs against osteoporosis, anti-cancer drugs, peptides, proteins, trophic factors and substances promoting bone growth, in particular growth factors and bone morphogenetic proteins.

The bone repair material further comprise an inorganic inhibitor for apatite dissolution and growth, preferably in the form of magnesium or pyrophosphate ions. The advantage is a stabilization of the formulation which prolongs its shelf life.

The bone repair material may further comprise an organic inhibitor for apatite dissolution and growth, preferably in the form of citrate ions, amino acids, peptides or proteins.

The bone repair material may be formulated in the form of a ready mixed putty material.

In a further embodiment the first and second component are in the form of a dry mixture to which the third component is to be added before use.

The third component may comprise blood, bone marrow, plasma, platelet-rich plasma or concentrated bone marrow cells.

In a further embodiment the second and third component are in the form of a nanocrystalline paste to which the first component is admixed before use.

In a further embodiment the third component comprises partly or fully a fluid extracted from the patient without or with additional processing, preferably in the form of blood, bone marrow, plasma, platelet-rich plasma or concentrated bone marrow cells.

The third component may comprise cells with osteogenic potential that have been cultivated and/or differentiated prior to their use. Said cells may be embryonic stem cells, stem cells, bone marrow cells or osteoblasts.

The bone repair may further comprise a radiopacifier. The radiopacifier may be in a liquid or in a solid form. Examples of powders are barium sulfate, strontium carbonate, zirconium oxide, bismuth oxide, metallic powders such as Tantalum, Tungsten, Gold, Platinum, or Titanium. Examples of liquids are liquids containing iode-based organic compounds such as: Iopamidol, lodixalonum, Iopentol, Iopramidum and Iotralonum.

The bone repair material according to the invention may be used for the preparation of an agent for the treatment of osteoporosis or bone tumors.

The mixture of the bone repair material may prepared directly in the operating room.

A further use of the bone repair material according to the invention consists in that blood, bone marrow, plasma, platelet-rich plasma or concentrated bone marrow cells are admixed as third component to a mixture of said first and second component. The main purpose of that use would be a putty material to be used as a bone repair material, i.e. to fill bone defects.

Preferably, the amount of liquid should be chosen in such a way that the amount of liquid can fill up all the gaps present within the powder and the granules. For example, if the apparent density of a mixture of β-TCP powder and dense granules is 0.8 g/cc, the amount of liquid that has to be added should be close to (3.1-0.8)/3.1=0.74 mL per gram of powder/granule mixture (3.1 g/cc is the absolute density of β-TCP). If the amount of liquid is lower than this ideal amount, the mixture is very brittle. If the amount of liquid is slightly larger than the ideal amount, the mixture becomes elastic, moldable, injectable, and sticky.

The useful amount of powder depends very much on the properties that the paste should have. Generally, an increase of the powder/granule ratio increases the elasticity, mouldability and injectability of the paste (keeping enough aqueous solution in the mixture, as described above for the preferred amount of liquid). So, preferably a balance should be found between good biological properties (enough granules to support cell anchorage and proliferation) and good paste properties (mouldability, elasticity, injectability).

Further objects and advantages of the invention will become apparent from the following specific examples.

EXAMPLES

Example 1

Several pastes were produced to investigate the effect of the content of the various components on the properties of the paste. The pastes were produced by mixing tricalcium phosphate powder with β3-TCP granules, and demineralized water. The tricalcium phosphate powder had a plastic limit of 1.01 mL water per gram of powder. The β-TCP granules had a diameter in the range of 0.180 and 0.5 mm (50% between 0.18 and 0.25 mm and 50% between 0.355 and 0.5 mm) and had an apparent density of 0.68-0.79 g/cc (depending on the granule size; a given amount of particles was packed in a graduated cylinder—the particle weight was divided by the apparent volume to determine the apparent density). The various compositions tested here are shown in Table 1.

The pastes were characterized by several means: stickiness (ability to stick to a surface), mouldability (ability to be shaped), and injectability (ability to be injected through a syringe). Additionally, the pastes were tested qualitatively by several people.

All 6 pastes had a similar stickiness and mouldability. However, pastes with more powder (samples 1-4 to 1-6) were injectable contrary to the paste with less powder (samples 1-1 to 1-3) which were not injectable at all. By hand, the paste with the largest amount of granule felt granular, whereas the other pastes were rather smooth.

TABLE 1 composition of the pastes obtained with tricalcium phosphate powder, β-TCP granules, and demineralized water.

| Paste # | Powder [g] | Granules [g] | Liquid [mL] |
|---|---|---|---|
| 1-1 | 2.00 (20.0%) | 2.15 (20.6%) | 2.00 (59.4%) |
| 1-2 | 2.00 (18.6%) | 2.35 (20.9%) | 2.20 (60.5%) |
| 1-3 | 2.00 (17.3%) | 2.55 (21.1%) | 2.40 (61.6%) |
| 1-4 | 2.00 (20.5%) | 1.92 (18.8%) | 2.00 (60.7%) |
| 1-5 | 2.00 (19.0%) | 2.09 (19.0%) | 2.20 (62.0%) |
| 1-6 | 2.00 (17.8%) | 2.27 (19.2%) | 2.40 (63.0%) |

The volume fraction (based on the weight and the theoretical density of each component) is given within parenthesis.

Example 2

The same powders and granules as those used in example 1 were used in this example. The paste was produced by combining a sterile mixture of 2 g tricalcium phosphate powder and 2.27 g β-TCP granules with 2.4 mL of human blood. The three components were mixed in a bowl with a spatula during one minute. The resulting paste was then moulded by hand and implanted into a model defect.

Example 3

Several pastes were produced to investigate the effect of the content of the various components on the properties of the paste. The pastes were produced by mixing tricalcium phosphate powder with β-TCP granules, and an aqueous magnesium chloride solution. The tricalcium phosphate powder had a plastic limit of 1.01 mL water per gram of powder. The β-TCP spherical granules had a diameter of 0.25-0.35 mm, and had an apparent density of 1.7-1.9 g/cc. All mixtures had a good mouldability, a low stickiness, and a good injectability. All mixtures felt very "granular" in the fingers.

TABLE 2 composition of the pastes obtained with tricalcium phosphate, β-TCP spherical granules and demineralized water.

| Paste # | Powder [g] | Granules [g] | Liquid [mL] |
|---|---|---|---|
| 2-1 | 2.0 (10.2%) | 12.5 (60.0%) | 2.0 (29.8%) |
| 2-2 | 2.0 (9.4%) | 13.4 (60.0%) | 2.2 (30.6%) |
| 2-3 | 2.0 (8.8%) | 14.3 (60.0%) | 2.4 (31.2%) |
| 2-4 | 2.0 (11.1%) | 10.6 (56.1%) | 2.0 (32.8%) |
| 2-5 | 2.0 (10.3%) | 11.4 (56.1%) | 2.2 (33.6%) |
| 2-6 | 2.0 (9.7%) | 12.2 (56.1%) | 2.4 (34.2%) |

The volume fraction (based on the weight and the theoretical density of each component) is given within parenthesis.

For the laboratory examples a spatula and a beaker were use for mixing the components. For production purposes mixing machines known in the art would be used. For those products which would be offered to the surgeon for mixing with blood an adequate mixing device could be added to a suitable package.

The invention claimed is:
1. A bone repair material comprising a mixture of:
  A) a first granular component having a diameter larger than 20 μm selected from the group consisting of: calcium phosphate, calcium pyrophosphate and calcium sulfate dihydrate;
  B) a second component consisting of apatite powder having a particle diameter smaller than 1 μm; and
  C) a third component comprising water or an aqueous solution;
  wherein the second component and the third component collectively represent at least 35 volume-% of the total bone repair material,
  wherein the bone repair material forms a paste when the first, second and third components are mixed together to form the mixture,
  wherein the bone repair material does not contain a hydrogel, and
  wherein the first granular component provides a scaffold on which bone cells can anchor and proliferate when the bone repair material is used to repair a defect in a bone filled with an aqueous body fluid.
2. The bone repair material according to claim 1, wherein the first component is selected from the group consisting of β-tricalcium phosphate, α-tricalcium phosphate, hydroxyapatite, tetracalcium phosphate, DCPD [dicalcium phosphate dihydrate ($CaHPO_4 \cdot 2H_2O$)], DCP [dicalcium phosphate ($CaHPO_4$)], OCP [octocalcium phosphate ($Ca_8H_2(PO_4)_6 \cdot 5H_2O$)], α-CPP [α-calcium pyrophosphate ($Ca_2P_2O_7$)], β-CPP [β-calcium pyrophosphate ($Ca_2P_2O_7$)], γ-CPP [γ-calcium pyrophosphate ($Ca_2P_2O_7$)], and CSD [calcium sulfate dihydrate ($CaSO_4 \cdot 2H_2O$)].
3. The bone repair material according to claim 1, wherein the diameter of said first granular component is larger than 100 microns.
4. The bone repair material according to claim 1, wherein the diameter of said first granular component is smaller than 200 microns.
5. The bone repair material according to claim 1, wherein the second component and the third component collectively represent 77 to 83 volume-% of the total bone repair material.

6. The bone repair material according to claim 1, wherein the apatite powder is selected from the group consisting of calcium-deficient hydroxyapatite, hydroxyapatite and fluoroapatite.

7. The bone repair material according to claim 1, wherein the first component comprises a mixture of several fractions of monodispersed granules of different size.

8. The bone repair material according to claim 7, wherein a size ratio of any two fractions of monodispersed granules of different size is larger than 1.5.

9. The bone repair material according to claim 1, wherein the granules of the first component are macroporous, with a pore diameter greater than 0.05 mm.

10. The bone repair material according to claim 1, wherein the granules of the first component have a porosity of less than 90%.

11. The bone repair material according to claim 1, wherein said granules of said first component have an apparent volume smaller than 30%.

12. The bone repair material according to claim 1, wherein the granules of the first component are spherical.

13. The bone repair material according to claim 1, wherein the granules of the first component are concave.

14. The bone repair material according to claim 1, wherein the apatite powder comprises deagglomerated powder particles.

15. The bone repair material according to claim 1, wherein the amount of said third component expressed in milliliters divided by the sum of the amounts of said first component and said second component expressed in grams is in the range of 0.1 to 0.7 mL/g.

16. The bone repair material according to claim 1, wherein the volume ratio between the third and the first component is in the range of 3.0 to 3.4.

17. The bone repair material according to claim 1 further comprising an additive increasing the surface charge of the particles present in the formulation.

18. The bone repair material according to claim 17, wherein said additive is a carboxylated compound having citrate or poly(carboxylated) ions.

19. The bone repair material according to claim 1, wherein said third component has an ionic strength of 0.15 M or higher.

20. The bone repair material according to claim 1 further comprising one or more drugs comprising a pharmaceutical or physiologically active substance useful in the treatment of bone defects or bone diseases.

21. The bone repair material according to claim 1 further comprising an inorganic inhibitor for apatite dissolution and growth, said inorganic inhibitor being magnesium or pyrophosphate ions.

22. The bone repair material according to claim 1 further comprising an organic inhibitor for apatite dissolution and growth, said organic inhibitor being citrate ions, amino acids, peptides or proteins.

23. The bone repair material according to claim 1, wherein the bone repair material is a ready mixed putty material.

24. The bone repair material according to claim 1, wherein said first component and second component are a dry mixture to which the third component is to be added before use.

25. The bone repair material according to claim 24, wherein the third component comprises blood, bone marrow, plasma, platelet-rich plasma or concentrated bone marrow cells.

26. The bone repair material according to claim 1, wherein said second component and third component are a nanocrystalline paste to which the first component is admixed before use.

27. The bone repair material according to claim 1, wherein said third component comprises a fluid extracted from the patient without or with additional processing, and wherein the fluid extracted from the patient is blood, bone marrow, plasma, platelet-rich plasma or concentrated bone marrow cells.

28. The bone repair material according to claim 1, wherein said third component further comprises cells with osteogenic potential that have been cultivated and/or differentiated prior to their use.

29. The bone repair material according to claim 28, wherein said cells are embryonic stem cells, stem cells, bone marrow cells or osteoblasts.

30. The bone repair material according to claim 1 further comprising a radiopacifier.

* * * * *